United States Patent
Vest et al.

(10) Patent No.: US 6,899,702 B2
(45) Date of Patent: May 31, 2005

(54) METHODS AND APPARATUS FOR ADMINISTERING INTRAVENOUS FLUIDS TO A PATIENT

(76) Inventors: Richard Donald Vest, 1241 Bischoff Rd., Granite City, IL (US) 62040; Deborah Susan Vest, 1241 Bischoff Rd., Granite City, IL (US) 62040

( * ) Notice: Subject to any disclaimer, the term of this patent is extended or adjusted under 35 U.S.C. 154(b) by 213 days.

(21) Appl. No.: 10/253,146

(22) Filed: Sep. 24, 2002

(65) Prior Publication Data

US 2004/0059287 A1 Mar. 25, 2004

(51) Int. Cl.$^7$ .............................................. A61M 31/00
(52) U.S. Cl. ......................... 604/500; 604/251; 604/80; 604/258
(58) Field of Search .............................. 604/246, 80, 81, 604/500, 518–520, 118, 122, 126, 257, 251–255, 258, 262, 284, 905, 403, 415, 411–413

(56) References Cited

U.S. PATENT DOCUMENTS

| | | | | |
|---|---|---|---|---|
| 4,236,515 A | * | 12/1980 | Genese | 604/81 |
| 4,237,879 A | * | 12/1980 | Genese | 604/81 |
| 4,252,116 A | * | 2/1981 | Genese et al. | 604/81 |
| 4,692,144 A | * | 9/1987 | Carpenter | 604/518 |
| 4,838,856 A | * | 6/1989 | Mulreany et al. | 604/65 |
| 5,059,173 A | * | 10/1991 | Sacco | 604/80 |

* cited by examiner

Primary Examiner—Cris L. Rodriguez
(74) Attorney, Agent, or Firm—Robert B. Reeser, III; Armstrong Teasdale LLP

(57) ABSTRACT

A method for administering intravenous fluids includes coupling a first fluid path in flow communication to a first fluid reservoir, coupling an inlet of a drip chamber in flow communication to the first fluid path, coupling an outlet of the drip chamber in flow communication to a patient supply path, and coupling a bypass fluid path in flow communication to the first fluid path. The method also includes directing fluid flow from the first fluid reservoir to the patient through the first fluid path and the drip chamber, and directing fluid flow from the first fluid reservoir to the patient through the bypass fluid path such that the drip chamber is bypassed.

18 Claims, 2 Drawing Sheets

METHODS AND APPARATUS FOR ADMINISTERING INTRAVENOUS FLUIDS TO A PATIENT

BACKGROUND OF THE INVENTION

This invention relates generally to intravenous fluid systems, and more particularly, to methods and apparatus for administering intravenous fluids to a patient.

Intravenous (IV) administration of fluids is an integral part of routine patient care, especially for those patients undergoing surgery. During surgery, invariably there is a need for fluids, including blood and saline, to be administered to a patient intravenously. In addition to providing fluids, there is a need to for IV administration of medications. While it is important that the correct fluids and medications are supplied into a vein through a continuous IV flow, delivery of the wrong blood type or medication may be life-threatening to a patient, and as such terminating the intravenous administration of the incorrect fluids and medications requires great immediacy.

At least some known IV systems include two fluid paths which each receive an intake of different fluids that may be supplied to a patient, and a single path for the administration of fluids. Specifically, during surgery the need arises for the administration of saline and/or blood, and as such known IV systems enable both a saline reservoir and a blood reservoir to supply fluids into a common drip chamber. The drip chamber, in combination with a variable resistance controller, allows the fluids to mix and facilitates accurate regulation of the rate of flow of the mixed fluids to the patient. If the patient has an allergic reaction to the blood, or if the blood is incorrectly cross-typed for the patient, tube clamps enable the flow from the blood reservoir to be stopped, such that an increased flow rate may be provided from the saline reservoir. The increased saline flow facilitates diluting the fluid mixture previously supplied to the patient and assists in hydrating the patient.

However, although no additional fluid enters the drip chamber from the blood reservoir when the tube clamp is positioned, any blood remaining in the IV system downstream from the tube clamp is still supplied to the patient, along with the increased flow rate of saline. Depending on the patient's reaction, the additional amount of incorrect fluid supplied to the patient may be life threatening to the patient. Accordingly, at least some known emergency procedures mandate that the IV system be uncoupled from the patient and either be flushed clean, or replaced with a new IV system. While such an emergency procedure ensures that the additional incorrect fluid is not supplied to the patient, replacing the IV system may be a time consuming and life-threatening event.

BRIEF DESCRIPTION OF THE INVENTION

In one aspect, a method is provided for administering fluids intravenously to a patient using an intravenous (IV) fluid supply system. The method comprises coupling a first fluid path in flow communication to a first fluid reservoir, coupling an inlet of a drip chamber in flow communication to the first fluid path, coupling an outlet of the drip chamber in flow communication to a patient supply path, and coupling a bypass fluid path in flow communication to the first fluid path. The method also comprises directing fluid flow from the first fluid reservoir to the patient through the first fluid path and the drip chamber, and directing fluid flow from the first fluid reservoir to the patient through the bypass fluid path such that the drip chamber is bypassed.

In another aspect of the invention, an intravenous (IV) fluid supply system for administering fluid to patient is provided. The IV fluid supply system includes a first fluid supply path including tubing configured to be coupled in flow communication to a first fluid reservoir, a second fluid supply path including tubing configured to be coupled in flow communication to a second fluid reservoir, and a drip chamber coupled in flow communication with the first fluid supply path and the second supply path. The drip chamber is also coupled to a patient supply path that includes tubing for routing fluids discharged from the drip chamber to the patient. The IV fluid supply system also includes a bypass fluid supply path that includes tubing including an upstream end and a downstream end. The tubing upstream end is coupled in flow to at least one of the first fluid supply path and the second fluid supply path for supplying at least one of the first fluid and the second fluid to the patient.

In a further aspect, an infusion system for administering intravenous fluid to a patient from a fluid reservoir is provided. The infusion system includes a drip chamber including an inlet and an outlet, a first fluid path including tubing coupled to the drip chamber inlet, wherein the first fluid path is configured to be coupled to a first fluid reservoir, and a patient supply path including tubing coupled in flow communication between the patient and the drip chamber outlet. The infusion system also includes a bypass fluid path including tubing having an upstream end that is coupled in flow communication to the first fluid path, and a downstream end that is coupled downstream from the drip chamber and in flow communication with the patient.

DETAILED DESCRIPTION OF THE INVENTION

Figure 1:
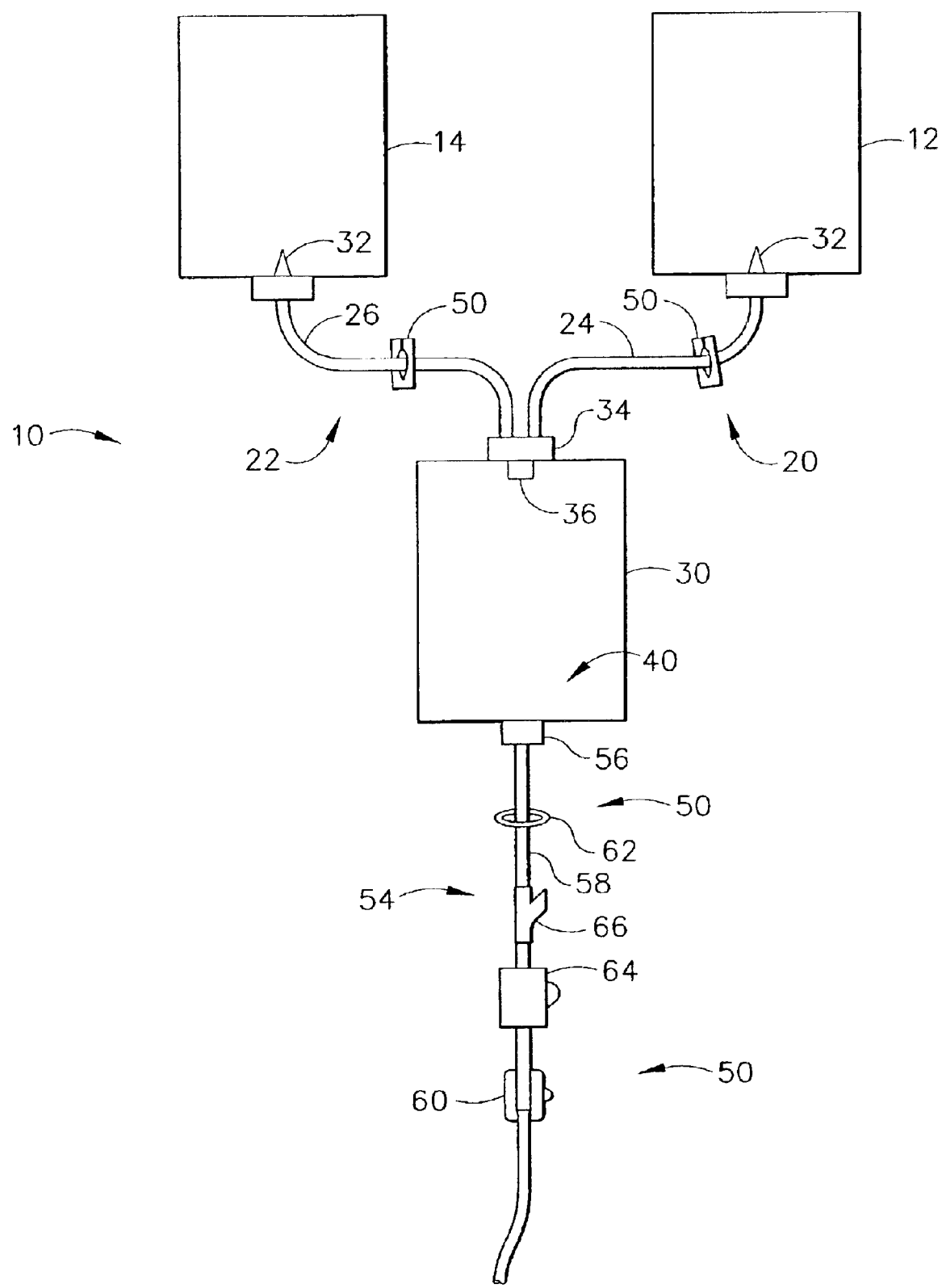
FIG. 1 is a schematic illustration of an exemplary known intravenous fluid supply system.

FIG. 1 is a known sterile intravenous fluid supply system 10 used to supply a fluid intravenously to a patient (not shown). In one embodiment, fluid supply system 10 is commercially available from Alaris Medical Systems, Inc., San Diego, Calif. In another embodiment, intravenous infusion system 10 is commercially available from Baxter Healthcare Corporation, Deerfield, Ill. 60015. More specifically, in the exemplary embodiment, fluid supply system 10 is coupled to a first fluid reservoir 12 and a second fluid reservoir 14, and is therefore used to selectively supply a first fluid, a second fluid, or a mixture of the first and second fluids to the patient. Reservoirs 12 and 14 store fluids to be supplied intravenously to the patient. In one embodiment, first fluid reservoir 12 is a collapsible bag type reservoir containing blood and second fluid reservoir 14 is a collapsible bag type reservoir containing saline.

Fluid supply system 10 includes a first supply tube assembly 20 and a second fluid supply tube assembly 22. In the exemplary embodiment, supply tube assemblies 20 and 22 are identical, and each includes a fluid passageway 24 and 26, respectively, for channeling fluid flow from each fluid reservoir 12 and 14 to a drip chamber 30. In the exemplary embodiment, fluid passageways 24 and 26 are formed by surgical tubing that is substantially clear, flexible, and compressible. More specifically, each reservoir 12 and 14 is positioned at a higher elevation with respect to the patient than drip chamber to enable gravitational force to cause fluid discharged from reservoirs 12 and 14 to flow towards drip chamber 30. In the exemplary embodiment, each fluid passageway 24 and 26 includes a sharpened inlet 32, known as a spike, for piercing each respective fluid reservoir 12 and 14 such that drip chamber 30 is coupled in flow communication to each fluid reservoir 12 and 14. In an alternative embodiment, fluid supply system 10 only includes first fluid supply tube assembly 20 coupled to fluid reservoir 12.

Drip chamber 30 is known in the art and includes a cap 34, a flow metering valve 36, and a hollow chamber 40. Chamber 40 is formed of a clear material to enable timing, and counting of drops of fluid supplied therethrough, such that the flow rate of fluid from flow metering valve 36 through chamber 40 may be verified. Flow metering valve 36 is formed integrally with cap 34 and permits fluid flow to be supplied through drip chamber 30 at a predetermined rate. Specifically, each drip chamber 30 is classified in drops per milliliter (mL), such that a certain number of drops discharged therethrough equals one mL of fluid.

Each supply tube assembly 20 and 22 includes at least one flow control device 50. Flow regulating devices 50 are used to regulate or stop the flow of intravenous fluid supplied through each supply tube assembly 20 and 22 to drip chamber 30. In the exemplary embodiment, flow regulating devices 50 are tube clamps that are coupled to each supply tube assembly 20 and 22 to selectively compress each respective fluid passageway 24 or 26 to stop fluid flow from one or both fluid reservoirs 12 and 14 to drip chamber 30.

In the exemplary embodiment, chamber 30 is configured to receive fluids from both fluid reservoirs 12 and 14. More specifically, if desired, fluid reservoirs 12 and 14 may simultaneously supply fluid to drip chamber 30. The fluids from both reservoirs 12 and 14 are mixed within chamber 30 prior to being discharged towards the patient through a patient supply tube assembly 54 that is coupled to an outlet 56 of drip chamber 30. More specifically, patient supply tube assembly 54 is coupled to drip chamber 30 in flow communication with both supply tube assemblies 20 and 22.

Patient supply tube assembly 54 is coupled in flow communication to a needle assembly (not shown) that is used to intravenously channel the fluids from fluid supply system 10 into the patient. In another embodiment, patient supply tube assembly 54 is coupled to a venopuncture site (not shown). In the exemplary embodiment, patient supply tube assembly 54 includes a fluid passageway 58 for channeling fluid flow from drip chamber 30 to the needle assembly for intravenous infusion into the patient. In the exemplary embodiment, surgical tubing forms fluid passageway 58.

A plurality of flow regulating devices 50 are coupled to patient supply tube assembly 54 downstream from drip chamber 30. Flow regulating devices 50 are used to regulate or stop the flow of intravenous fluid from drip chamber 30 to the needle assembly. For example, in the exemplary embodiment, system 10 includes at least one roller clamp 60 that is clamped to tubing 54 such that moving the roller along tubing 54 adjusts a rate of fluid flow through passageway 54. In another embodiment, system 10 includes at least one slide clamp 62 which when moved will completely occlude tubing 54 to prevent fluid flow therethrough. A filter 64 and an injection port 66 are also coupled in flow communication between drip chamber 30 and the needle assembly. In one embodiment filter 64 is a 180-micron filter. In another embodiment, filter 64 is a variably sized micron filter known in the art.

In use, fluid supply system 10 is positioned at a higher elevation than the patient, and gravity forces fluid from both the first and second fluid reservoirs 12 and 14, towards respective supply tube assemblies 20 and 22. More specifically, fluid flow through either fluid passageway 24 or 26 may be terminated by engaging a respective flow regulating device coupled to either first supply tube assembly 20 or second fluid supply tube assembly 22.

Gravity forces the fluid into drip chamber 30 wherein the fluid may be discharged from drip chamber 30 into patient supply tube assembly 54 at a predetermined flow rate. If the patient has an allergic reaction to the blood, or if the blood is incorrectly cross-typed for the patient, flow regulating devices 50 enable the flow from the undesired fluid reservoir 12 or 14 to be stopped, such that an increased flow rate may be provided from the other fluid reservoir 14 or 12. The increased fluid flow from the other reservoir 12 or 14 diluting the fluid mixture previously supplied to the patient and assists in hydrating the patient. However, any fluid remaining within system 10 that is downstream from the flow regulating device 50 is still supplied to the patient. For example, any fluid within the drip chamber 30 or within patient supply tube assembly 54 will still be supplied to the patient. Depending on the patient's reaction, the additional amount of incorrect fluid supplied to the patient may be life-threatening to the patient.

Figure 2:
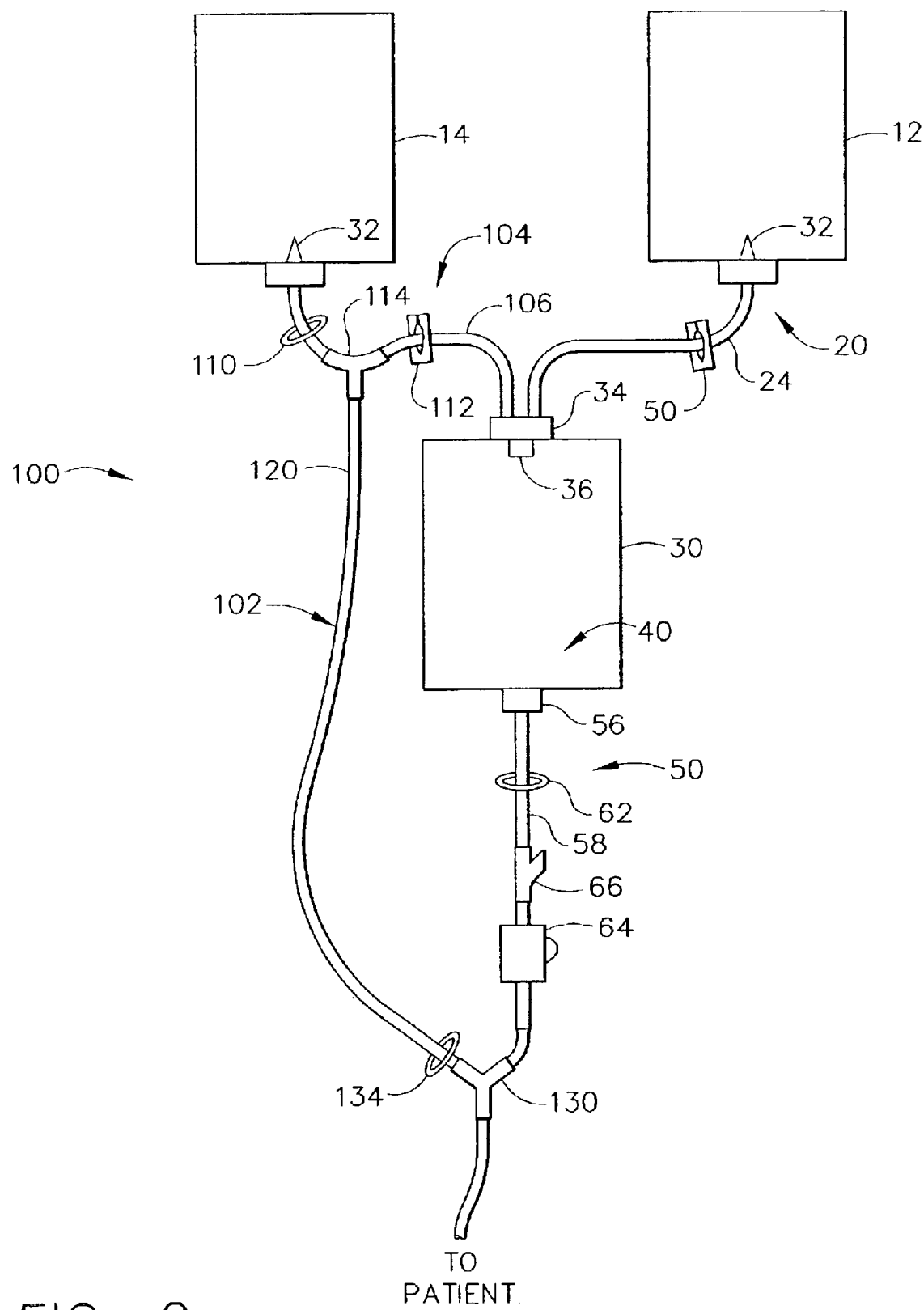
FIG. 2 is an intravenous fluid supply system, including a bypass fluid supply path.

FIG. 2 is an intravenous fluid supply system 100, including a bypass fluid supply path 102. Intravenous fluid supply system 100 is substantially similar to intravenous fluid supply system 10 (shown in FIG. 1) and components of system 10 that are identical to components of fluid supply system 100 are identified in FIG. 2 using the same reference numerals used in FIG. 1. Accordingly, fluid supply system 100 includes drip chamber 30, patient supply tube assembly 54, and first supply tube assembly 20. Fluid supply system 100 also includes bypass fluid supply path 102 and a second supply tube assembly 104.

Second supply tube assembly 104 includes a fluid passageway 106 for channeling fluid flow from fluid reservoir 14 to drip chamber 30. In the exemplary embodiment, surgical tubing that is substantially clear, flexible, and compressible forms fluid passageway 106.

Supply tube assembly 104 includes an upstream flow regulating device 110, a downstream flow regulating device 112, and a junction 114 that is positioned therebetween. More specifically, flow regulating device 112 is positioned between junction 114 and drip chamber 30 to stop fluid flowing through junction 114 towards drip chamber 30, and flow regulating device 110 is positioned between junction 114 and fluid reservoir 14 to stop fluid flowing from fluid reservoir 14 into supply tube assembly 104.

Junction 114 couples bypass fluid supply path 102 to supply tube assembly 104 in flow communication. In the exemplary embodiment, junction 114 is a Y-fitting. As described in more detail below, bypass fluid supply path 102 includes a fluid passageway 120 for channeling fluid flow from fluid reservoir 14 to the patient without the fluid flowing through drip chamber 30. In the exemplary embodiment, surgical tubing that is substantially clear, flexible, and compressible forms fluid passageway 120. Accordingly, flow regulating device 112 prevents fluid from flowing through junction 114 towards drip chamber 30, and when closed, fluid discharged from fluid reservoir 14 is directed into bypass fluid supply path 102 if flow regulating device 114 is open.

Fluid passageway 120 extends in flow communication from junction 114 and is coupled in flow communication to the patient downstream from drip chamber 30. More specifically, in the exemplary embodiment, bypass fluid supply path 102 is coupled to a downstream junction 130 that is coupled in flow communication to both bypass fluid supply path 102 and to patient supply tube assembly 54. Fluid passageway 120 includes a flow regulating device 134 used to prevent fluid from flowing from passageway 120 to the patient through junction 130. Flow regulating device 134, as described in more detail below, also enables bypass fluid supply path 102 to be primed during use of system 100.

In use, fluid supply system 100 is positioned at a higher elevation than the patient. Fluid path 104 is coupled in flow communication to an inlet of drip chamber 30. An outlet of drip chamber 30 is coupled in flow communication to patient supply path 54. Bypass fluid path 102 is coupled in flow communication to fluid path 104. Gravitational forces cause fluid to drain from both the first and second fluid reservoirs 12 and 14, towards respective supply tube assemblies 20 and 102, and towards bypass fluid supply path 102. More specifically, after system 100 is coupled to a patient, initially a flow regulating device 50 is clamped to first supply tube assembly 20 to prevent flow of fluid from fluid reservoir 12. Additionally, upstream flow regulating device 110 and downstream flow regulating device 112 are both opened to enable fluid to flow from reservoir 14 into drip chamber 30 through supply tube assembly 104, and into bypass fluid passageway 120. More specifically, drip chamber 30 may be used to prime system 100 such that fluid begins flowing into tube assembly 104 and bypass fluid passageway 120.

After fluid is supplied to the patient through bypass fluid passageway 120, flow regulating device 134 is used to prevent additional fluid from flowing from passageway 120 to the patient through junction 130. More specifically, flow regulating device 134 is coupled to passageway 120 immediately upstream from junction 130 such that passageway 120 is substantially filled with intravenous fluid between flow regulating device 134 and junction 114.

Gravity forces the fluid into drip chamber 30 from fluid reservoir 14. If desired, flow regulating devices 50 and 112, respectively, may be coupled to first supply tube assembly 20 and second supply tube assembly 104, respectively, to supply only fluid from first reservoir 12, only fluid from second reservoir 14, or a mixture of the fluid from both reservoirs 12 and 14 to the patient through drip chamber 30.

If the patient has an adverse reaction to the first fluid, flow regulating device 134 is uncoupled from passageway 120, and second supply tube assembly flow regulating device 112 is clamped to prevent the second fluid from flowing towards the drip chamber. Furthermore, a flow regulating device 50 is also clamped to patient supply tube assembly 54, upstream from junction 130 to prevent any fluid upstream from junction 130 being supplied to the patient. More specifically, fluid upstream from junction 130 is prevented from being supplied to the patient, and as such, the adverse effects of the patient can be reversed more quickly because the increased fluid flow from second reservoir 14 facilitates diluting the fluid previously supplied to the patient through drip chamber 30. In addition, the fluid flow from second reservoir 14 also facilitates hydrating and stabilizing the patient with the second fluid.

The above-described intravenous fluid supply systems are cost-effective and highly reliable. The fluid supply system includes a bypass fluid supply path that enables fluid to be delivered to the patient while bypassing the drip chamber. More importantly, the bypass fluid supply path provides a means for supplying only one fluid to the patient, without flushing the fluid supply system, and without allowing the remaining fluid within the fluid supply system to enter the patient. Thus, if a saline reservoir is coupled to the fluid supply system with a blood reservoir, if the patient has an adverse reaction to the blood received, the fluid supply system can be quickly configured such that only the saline is supplied to the patient to facilitating diluting the fluids that the patient already received. As a result, the intravenous fluid supply system facilitates delivering fluids to a patient in a cost-effective and reliable manner.

Exemplary embodiments of an intravenous fluid supply system are described above in detail. The systems are not limited to the specific embodiments described herein, but rather, components of each system may be utilized independently and separately from other components described herein. Each intravenous fluid supply system component can also be used in combination with other intravenous fluid supply system components.

While the invention has been described in terms of various specific embodiments, those skilled in the art will recognize that the invention can be practiced with modification within the spirit and scope of the claims.

What is claimed is:

1. A method for administering fluids intravenously to a patient using an intravenous (IV) fluid supply system, said method comprising:
coupling a first fluid path in flow communication to a first fluid reservoir;
coupling a second fluid path in flow communication to a second fluid reservoir;
coupling an inlet of a drip chamber in flow communication to the first and second fluid paths;
coupling an outlet of the drip chamber in flow communication to a patient supply path;
coupling a bypass fluid path in flow communication to only the first fluid path;
directing fluid flow from the first fluid reservoir to the patient through the bypass fluid path such that the drip chamber is bypassed.

2. A method in accordance with claim 1 wherein directing fluid flow from the first fluid reservoir to the patient through the bypass fluid path comprises directing fluid flow from the first fluid reservoir to the patient through at least one junction connected in flow communication to the patient fluid supply path and the bypass fluid pass, downstream from the drip chamber.

3. A method in accordance with claim 1 wherein directing fluid flow from the first fluid reservoir to the patient through the bypass fluid path comprises postioning a fluid controller to selectively control fluid flow through the bypass fluid path.

4. A method in accordance with claim 1 wherein directing fluid flow from the first fluid reservoir to the patient through the first fluid path and the drip chamber further comprises positioning a fluid controller to selectively control fluid flow discharged from the drip chamber into the patient fluid supply path.

5. A method in accordance with claim 1 wherein coupling a bypass fluid path in flow communication to the first fluid path further comprises coupling the bypass fluid path in flow communication to the first fluid path using a Y-connection such that at least one fluid controller is upstream from the Y-connection, and such that at least one controller is downstream from the Y-connection within the first fluid path and within the bypass fluid path.

6. An intravenous (IV) fluid supply system for administering fluid to patient, said IV fluid supply system comprising:

a first fluid supply path comprising tubing configured to be coupled in flow communication to a first fluid reservoir;

a second fluid supply path comprising tubing configured to be coupled in flow communication to a second fluid reservoir;

a drip chamber coupled in flow communication with said first fluid supply path and said second supply path, and coupled to a patient supply path comprising tubing for routing fluids discharged from said drip chamber to the patient; and a bypass fluid supply path comprising tubing comprising an upstream end and a downstream end, said upstream tubing end coupled in flow communication to only one of said first fluid supply path and said second fluid supply path for supplying at least one of the first fluid and the second fluid to the patient.

7. An IV fluid supply system in accordance with claim 6 wherein said bypass fluid supply path tubing downstream end coupled in flow communication to the patient downstream from said drip chamber.

8. An IV fluid supply system in accordance with claim 6 wherein said bypass fluid supply path for supplying at least one of the first fluid and the second fluid to the patient by bypassing said drip chamber.

9. An IV fluid supply system in accordance with claim 6 further comprising at least one fluid controller for selectively controlling fluid flow through said bypass fluid supply path.

10. An IV fluid supply system in accordance with claim 6 further comprising at least one junction downstream from said drip chamber, said patient supply path and said bypass fluid supply path coupled in flow communication to said at least one junction.

11. An IV fluid supply system in accordance with claim 10 further comprising at least one fluid controller for selectively controlling fluid flow from said drip chamber to said at least one junction.

12. An IV fluid supply system in accordance with claim 10 further comprising at least one fluid controller for selectively controlling fluid flow from said drip chamber to said at least one junction, said at least one fluid controller coupled to said patient supply path between said drip chamber and said at least one junction.

13. An infusion system for administering intravenous fluid to a patient from a fluid reservoir, said infusion system comprising:

a drip chamber comprising an inlet and an outlet;

a first fluid path comprising tubing coupled to said drip chamber inlet, said first fluid path configured to be coupled to a first fluid reservoir;

a second fluid supply path comprising tubing configured to be coupled in flow communication to a second fluid reservoir;

a patient supply path comprising coupled in flow communication between the patient and said drip chamber outlet; and a bypass fluid path comprising tubing comprising an upstream end coupled in flow communication to only the first fluid path, and a downstream end coupled downstream from the drip chamber in flow communication with the patient.

14. An infusion system in accordance with claim 13 further comprising at least one junction downstream from said drip chamber, said at least one junction coupled in flow communication with said patient supply path and said bypass fluid path.

15. An infusion system in accordance with claim 14 further comprising at least one fluid controller for selectively controlling fluid flow from said drip chamber to said at least one junction, said at least one fluid controller coupled to said patient supply path between said drip chamber and said at least one junction.

16. An infusion system in accordance with claim 14 further comprising at least one fluid controller for selectively controlling fluid flow through said bypass fluid supply path.

17. An infusion system in accordance with claim 14 wherein said at least one junction downstream from said drip chamber comprises a Y-fitting.

18. An infusion system in accordance with claim 14 wherein said bypass fluid supply path for supplying fluid to said patient without fluid entering said drip chamber, said bypass fluid supply path coupled to said first supply with at least one connector.

* * * * *